US006421130B1

(12) United States Patent
Phillion

(10) Patent No.: US 6,421,130 B1
(45) Date of Patent: Jul. 16, 2002

(54) CONSTANT VOLUME GAS CELL OPTICAL PHASE-SHIFTER

(75) Inventor: Donald W. Phillion, Dublin, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/282,009

(22) Filed: Mar. 29, 1999

(51) Int. Cl.[7] .................................... G01B 9/02
(52) U.S. Cl. .................................... 356/450
(58) Field of Search .................................... 356/517, 450, 356/484, 485, 486

(56) References Cited

U.S. PATENT DOCUMENTS

| | | | | |
|---|---|---|---|---|
| 3,035,482 A | * | 5/1962 | Kinder | 250/201 |
| 3,680,963 A | * | 8/1972 | Edwards et al. | 356/517 |
| 3,723,009 A | * | 3/1973 | Clark | 356/517 |
| 4,571,082 A | * | 2/1986 | Downs | 356/491 |
| 4,813,783 A | * | 3/1989 | Torge | 356/498 |
| 5,483,343 A | * | 1/1996 | Iwamoto et al. | 356/484 |

* cited by examiner

*Primary Examiner*—Frank G. Font
*Assistant Examiner*—Andrew H. Lee
(74) *Attorney, Agent, or Firm*—L. E. Carnahan; Alan H. Thompson

(57) ABSTRACT

A constant volume gas cell optical phase-shifter, particularly applicable for phase-shifting interferometry, contains a sealed volume of atmospheric gas at a pressure somewhat different than atmospheric. An optical window is present at each end of the cell, and as the length of the cell is changed, the optical path length of a laser beam traversing the cell changes. The cell comprises movable coaxial tubes with seals and a volume equalizing opening. Because the cell is constant volume, the pressure, temperature, and density of the contained gas do not change as the cell changes length. This produces an exactly linear relationship between the change in the length of the gas cell and the change in optical phase of the laser beam traversing it. Because the refractive index difference between the gas inside and the atmosphere outside is very much the same, a large motion must be made to change the optical phase by the small fraction of a wavelength that is required by phase-shifting interferometry for its phase step. This motion can be made to great fractional accuracy.

20 Claims, 2 Drawing Sheets

CONSTANT VOLUME GAS CELL OPTICAL PHASE-SHIFTER

CONSTANT VOLUME GAS CELL OPTICAL PHASE-SHIFTER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to optical phase-shifters, particularly to optical phase-shifting interferometry, and more particularly to a constant volume gas cell optical phase-shifter which can produce motions which are accurate to about 5 Å.

Optical phase-shifting is utilized in a variety of applications, and particularly in interferometry. Present commercial technology for phase-shifting interferometry uses three piezoelectric transducers (PZTs) on a mirror, or a long fiber optic cable that is stretched by a piezoelectric transducer. In the PZT/mirror arrangement, for example, A $\pi/4$ phase step at the optical wavelength of 5320 Å requires that the mirror be longitudinally displaced by 332.5 Å. These motions can be made accurately enough for routine optical fabrication. However, in order to do interferometry to an accuracy of 1 Å in the surface height, these motions must be accurate to about 5 Å, and such accuracy is very difficult with existing technology.

The present invention provides a phase-shifting arrangement that can easily achieve the accuracy required for interferometry, and is inexpensive to fabricate. The invention involves a constant volume gas cell optical phase-shifter which has the capability to make the required phase steps accurately. The constant volume gas cell can make very precise phase steps that are extremely constant across the beam wavefront. As a beam travels thorough a gas filled tube of the cell the length of the tube can be changed, thus changing the optical path length of the beam traversing the cell. Because the cell is constant volume, the pressure, temperature, and density of the contained gas do not change as the cell changes length. This means that there is an exactly linear relationship between the changes in length of the gas cell and the change in optical phase of the beam traversing it. The constant volume gas cell phase-shifter is simple to construct and provides very precise phase steps as the length of the cell is changed.

SUMMARY OF THE INVENTION

It is an object of the present invention to provide an improved optical phase-shifter.

A further object of the invention is to provide an optical phase-shifter having an accuracy compatible for interferometry applications.

A further object of the invention is to provide an optical phase-shifter which is of simple construction, but which produces high accuracy.

Another object of the invention is to provide an improved optical phase-shifter which involves a constant volume gas cell.

Another object of the invention is to provide a constant volume gas cell which can make very precise phase steps that are extremely constant across a beam wavefront.

Another object of the invention is to provide a constant volume gas cell optical phase-shifter wherein precise phase steps are accomplished by changing the length of the gas cell through which a beam traverses, the changing the optical path length of the beam.

Other objects and advantages of the present invention will become apparent from the following description and accompanying drawings. The invention is directed to a constant volume gas cell optical phase-shifter which can make very precise phase steps that are extremely constant across the beam wavefront. The cell is basically composed of three concentric tubes, two of which are interconnected and positioned such that the inner of the interconnected two tubes moves within the third tube and the third tube moves within the outer of the interconnected two tubes, with each tube being provided with a seal at one end thereof, and with an equalizer passage between the third and outer tubes, and between the two connected tubes and the exterior of the cell. The inner tube and the third tube and a portion of the outer tube are filled with a gas, such as air, for example, at a pressure different than atmospheric. The inner and third tubes are provided with optical windows at an end opposite the seals. The gas within the three tubes is at a constant volume and passes from the third tube to the outer tube or vice versa upon the third tube being moved with respect to the connected inner and outer tubes, thus the inner and third tubes are full of gas at all times, and the volume of gas in the outer tube changes as the third tube and interconnect two tubes move with respect to one another. Thus, with a beam, such as a laser beam, traversing the third and inner tubes of the cell, as the length of the cell changes (two move with respect to each other), the optical path length of the laser beam traversing the cell changes. Since the gas in the cell is at a constant volume, there is an exact linear relationship between the change in length of the gas cell and the change in optical phase of the laser beam traversing it. Thus, the cell can be designed, for example, such that a change or motion of 10 millimeter in cell length cause one wavelength change in the optical path. Thus, this motion in cell length can be made to great wavelength fractional accuracy, such as required by phase-shifting interferometry for its phase step.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention involves a constant volume gas cell optical phase-shifter which can make very precise phase steps by accurately changing the length of the optical path of a beam traversing the cell. The cell contains a constant volume of gas, at a pressure different from atmospheric pressure, regardless of the change in length of the cell and thus the pressure, temperature, and density of the contained gas do not change as the cell changes length. This results in an exactly linear relationship between the change in length of the gas cell and the change in optical phase of a laser beam, for example, traversing the cell. Because the refractive index between the gas inside and the atmosphere outside is very small, a large motion must be made to change the optical phase by a small fraction of a wavelength that is required by phase-shifting interferometry for its phase step. This motion can be made to great fractional accuracy.

By way of example, if one desires that a motion of 10 millimeters cause one wavelength change in the optical path, such means that the refractive index difference should be $n_2-n_1=\lambda/(10\ \text{mm})=\pm5.32\times10^{-5}$ for $\lambda=0.532\times10^{-3}$. Since n=1.000294 at normal pressure, the pressure difference would be ±1.37.5 Torr.

Figure 1:
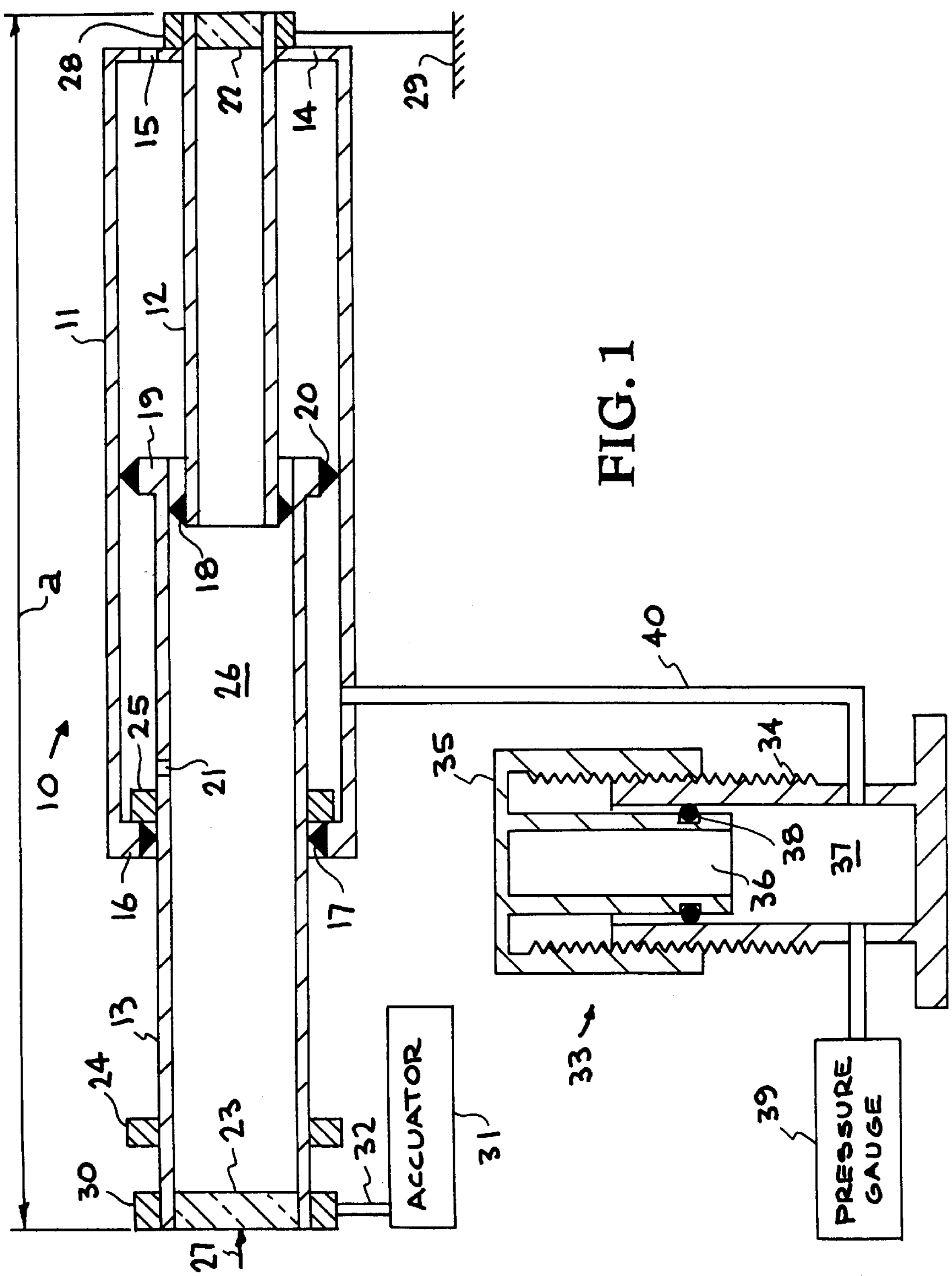
FIG. 1 illustrates in cross-section an embodiment of a constant volume gas cell optical phase-shifter, in accordance with the present invention, and shown in its expanded condition.
Figure 2:
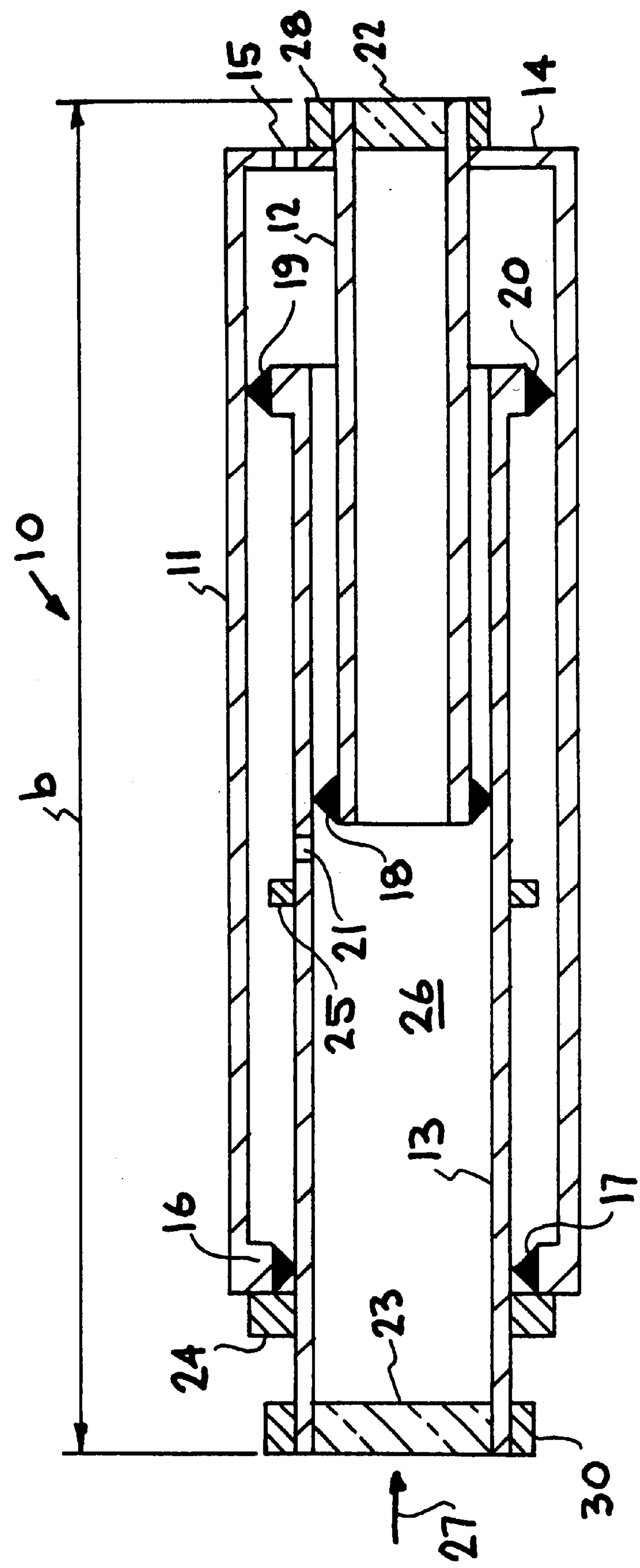
FIG. 2 is a cross-sectional view of the FIG. 1 embodiment in its contracted condition.

Referring now to the drawings, FIGS. 1 and 2 illustrate in cross-section an embodiment of a constant volume gas cell with the length of the cell being expanded in FIG. 1 and contracted in FIG. 2, and with the actuator and pressurization unit omitted in FIG. 2. As shown, the constant volume gas cell, generally indicated at 10, includes three concentric members or tube sections, a first or outer tube 11, a second or inner tube 12, and a third tube 13. Tubes 11 and 12 are connected at one end by a plate or member 14 having an aperture or equalizer passage 15 therein. Tube 11 is provided at the opposite end with an inwardly directed flange 16 having a seal assembly 17 secured to the flange. Tube 12 is provided with a seal assembly 18. If desired the flange could be omitted and the seal assembly attached to an inner end surface of tube 11. Tube 13 extends within outer tube 11 and around inner tube 12 and includes an inwardly extending flange 19 and seal assembly 20. Flange 19 can be omitted with the seal assembly 20 secured to an inner end surface of tube 13. Tube 13 is provided with an aperture or equalizer passage 21. Each of tubes 12 and 13 are provided at the outer ends (opposite the seal assemblies) with optical windows 22 and 23. Tube 13 is provided with a stop member or plate 24 attached to tube 13 and located so as to prevent excessive inward movement of tube 13 within tube 11 such that the equalizer passage 21 does not move past seal assembly 18 of tube 12. Also, a stop member or plate 25 is attached to and located on tube 13 to prevent excessive outward movement of tube 13 to prevent equalizer passage 21 from moving past seal assembly 17 of tube 11. The length of cell 10 in its expanded condition as shown in FIG. 1 is indicated by arrow a, while the length as shown in FIG. 2 in its contracted condition is indicated by the arrow b. Thus, the distance or travel range which the tube 13 can move with respect to the tubes 11–12 is equal to a–b, which may be in the range of up to 10 mm. Optimally, the minimum length is roughly twice the travel range and the maximum length is roughly three times the travel range.

In operation, with the interior of tubes 12 and 13 and the area of tube 11 intermediate seal assemblies 17 and 20 filled with a constant volume of gas, such as air indicated at 26, at a pressure different than atmospheric (external) pressure, and a beam, such as a laser beam, indicated at 27 travels from left to right passes through window 23, tube 13, tube 12, and window 22 at a certain optical path length. By sliding the tube 13 into tube 11 and around tube 12, or vice versa, the length of the cell, is changed from a distant (a) of FIG. 1 to a distance or length (b) of FIG. 2, thus changing the optical path length of beam 27. As the length from window 22 to window 23 changes, gas passes from within tube 13 via passage 21 to tube 11, or vice versa, whereby there remains a constant volume of gas within the cell. As the seal assembly 20 of tube 13 moves with respect to plate 14 air in tube 11 equalizes with external air via passage 15. Thus, movement of tube 13 with respect to tubes 11–12 does not change the gas pressure within the cell 10. Because the volume of the enclosed gas does not change as the length of the cell 10 is changed, the temperature and density of gas 26 within the cell does not change. In order for the volume of enclosed gas to remain fixed as the length of the cell is changed, the cross-sectional area of the cylinder of gas within tube 13 (between window 23 and seal assembly 18 of tube 12) must equal the cross sectional area of the annulus of gas in tube 11 (located between seal assembly 17 of tube 11 and seal assembly 20 of tube 13). The end stops 25, functions to prevent tube 13 from being pulled to the left as seen in FIG. 1, so as not to be located within tube 11 and around tube 12 and thus preventing passage 21 from moving past seal assembly 17 to break the seal gas enclosure. Similarly, end stop 24 prevents tube 13 from moving to the right, as seen in FIG. 2, such that the passage 21 is moved past the seal assembly 18 of tube 12, and thus break the sealed gas enclosure with cell 10.

In actual practice, the cell 10 would be mounted, for example, such that interconnected tube 11 and 12 would be held fixed, and an actuator means would selectively move tube 13. Various mechanisms may be utilized and are schematically illustrated in FIG. 1, wherein a retainer ring or member 28 is secured to tube 11 and which is attached to a fixed structure 29, and a drive ring or member 30 is secured to tube 13 and which is attached to a linear actuator 31 by an arm or member 32, whereby tube 13 can be moved with respect to tubes 11 and 12, as described above.

A modest overpressure in the gas cell 10 can be chosen to make the motion for a phase step by whatever is desired. By making the motion be millimeters rather than hundreds of angstroms (332.5 Å for a $\pi/4$ phase step in reflection for $\lambda$=5320 Å), the height accuracy of conventional translation stages may be utilized. Since this is a constant volume cell, no mechanical work can be done and regardless of the pressure to which the gas cell is fill, there is no tendency for the two tube assemblies to move either further apart or closer together. And, of course, the pressure will not change as the two tube assemblies are moved relative to each other.

As an example, for a tenth of an atmosphere over-pressure of the gas in the tubes and wavelength of 5320 Å, the cell would need to be lengthened 2.277 mm for a $\pi/4$ phase step (n=1.000292 for air at STP). The cell could be pressurized by adjusting a pressurization unit generally indicated at 33. The pressurization unit 33 basically includes a threaded body member 34, a threaded cap member 35 having an internal hollow section 36 which extends into an interior chamber 37 body member 34, an o-ring seal 38 between hollow section 36 and body member 34, a pressure gauge 39 connected to chamber 37 and a small tube 40 connecting chamber 37 with the interior of tube 11 intermediate seals 17 and 20. The cap member 35 would be screwed in to decrease the volume by 10%, and would be unscrewed and removed to come back to atmospheric pressure and then screwed back in again to repressurize. The cylindrical O-ring seal 38 would maintain the gas seal as the cap 35 is screwed in. The pressure could be set by how far the cap 35 was screwed in.

While the gas cell has been illustrated and described using cylindrical or tubular members, members of other configurations, such as square, triangular, or oblong, etc. may be utilized, provided seal assemblies can be effectively provided for other configurations.

It has thus been shown that the present invention provides a constant volume gas cell optical phase-shifter having the following advantages: 1) very precise phase steps, 2) phase steps very precisely the same across the beam wavefront, 3) physically compact, and 4) simple and inexpensive to manufacture. Thus, the constant volume gas cell of the present invention is particularly useful for phase-shifting interferometry, as the movement to produce phase steps can be made to great fractional accuracy.

While a specific embodiment of the invention has been illustrated and described, and specific parameters, etc. have been set forth they exemplify and explain the principles of the invention, such are not intended to be limiting. Modifications and changes may become apparent to those skilled in the art and it is intended that the invention be limited only by the scope of the appended claims.

The invention claimed is:

1. A constant volume gas cell, comprising:

a first member having a window therein;

a second member having a window therein;

said first member being moveable with respect to said said second member, wherein said windows are in optical alignment;

said second member being in fluid communication with atmosphere;

said first and second members being in fluid communication via a passage in said first member;

said first and second members containing a quantity of gas located intermediate said windows and at a pressure different from atmospheric pressure and of a constant volume;

seal means for preventing leakage of said quantity of gas from within said first and second members; and means for moving said first member with respect to said second member.

2. The gas cell of claim 1, additionally including stop means for limiting movement of said members.

3. The gas cell of claim 1, wherein said first and second members comprise a pair of tubular assemblies.

4. The gas cell of claim 3, wherein a first of said tubular assemblies includes a pair of concentric tubes connected at one end, said window being located in an inner tube of said pair of concentric tubes, and wherein a second of said pair of said tubular assemblies comprises a single tube positioned to extend intermediate said pair of concentric tubes.

5. The gas cell of claim 4, wherein said second of said members being in fluid communication with atmosphere comprising an outer tube of said pair of concentric tubes and having a fluid passage therein.

6. The gas cell of claim 4, wherein said passage providing fluid communication between said members is located in said single tube.

7. The gas cell of claim 4, wherein said windows comprise optical windows, with said window of said second member being located in an outer end of said inner tube, and said window of said first member being located in an outer end of said single tube.

8. The gas cell of claim 4, wherein said seal means comprises three seal assemblies, a first of said seal assemblies being mounted to an inner end of said single tube, a second of said seal assemblies mounted to an inner end of said inner tube, and a third of said seal assemblies being mounted to an end of an outer tube of said pair of concentric tubes opposite said one end connected to said inner tube.

9. The gas cell of claim 4, wherein said pair of concentric tubes are connected by a plate, and wherein said plate includes a passage for providing said fluid communication with the atmosphere.

10. The gas cell of claim 4, wherein said single tube is provided with a pair of spaced stop members, whereby maximum movement of said single tube with respect to said pair of concentric tubes is controlled by location of said stop members on said single tube.

11. The gas cell of claim 1, in combination with an interferometer, and wherein movement of said members with respect to one another causes change in an optical path length of a light beam passing through said gas located intermediate said windows of said first and second members.

12. The gas cell of claim 1, additionally including means for changing pressure of said quality of gas.

13. An optical phase-shifter, comprising:

a constant volume gas cell;

said gas cell including a pair of tubular assemblies containing a constant volume of gas therein having a pressure different from atmospheric pressure;

each of said pair of tubular assemblies including an optical window at one end thereof;

said optical windows being in alignment with each other;

means for providing said gas to pass between said tubular assemblies;

one of said tubular assemblies being moveable with respect to the other;

wherein movement of said one tubular assembly creates a change in optical path length between said windows, producing a phase shift in a light beam passing therethrough.

14. The optical phase-shifter of claim 13, wherein said constant volume gas cell, additionally includes means for moving said tubular assemblies with respect to each other.

15. The optical phase-shifter of claim 13, wherein said pair of tubular assemblies are constructed so that movement thereof does not change the temperature, pressure, or density of the gas therein.

16. The optical phase-shifter of claim 13, additionally including means for stopping movement of said tubular assemblies.

17. The optical phase-shifter of claim 13, additionally including seal means for preventing leakage of said gas therefrom.

18. The optical phase-shifter of claim 13, additionally including means for changing pressure of said gas in said tubular assemblies.

19. The optical phase-shifter of claim 13, wherein said means for providing said gas to pass between said tubular assemblies comprises a passage in one of said tubular assemblies.

20. The optical phase-shifter of claim 13, additionally including a passage in one of said tubular assemblies for providing fluid communication with an exterior of said one tubular assembly.

* * * * *